United States Patent
Hamilton et al.

(10) Patent No.: US 6,423,016 B1
(45) Date of Patent: Jul. 23, 2002

(54) SYSTEM AND METHOD FOR EVALUATING LABOR PROGRESS DURING CHILDBIRTH

(75) Inventors: Emily Hamilton, Verdun; Mario Boisclair, Montreal; Ebi Kimanani, Beaconsfield; Bruno Bendavid, Montreal, all of (CA)

(73) Assignee: LMS Medical Systems Ltd., Montreal (CA)

( * ) Notice: Subject to any disclaimer, the term of this patent is extended or adjusted under 35 U.S.C. 154(b) by 38 days.

(21) Appl. No.: 09/589,657

(22) Filed: Jun. 8, 2000

(51) Int. Cl.[7] ........................ A61B 5/103; A61B 5/117
(52) U.S. Cl. .................................................. 600/588
(58) Field of Search ........................... 600/588, 300; 128/897, 898

(56) References Cited

U.S. PATENT DOCUMENTS

| 5,497,317 A | 3/1996 | Hawkins et al. |
| 5,851,188 A | 12/1998 | Bullard et al. |

FOREIGN PATENT DOCUMENTS

| EP | 0 384 339 | 8/1990 |
| WO | WO 98/49942 | 11/1998 |
| WO | WO 00/01117 | 1/2000 |

OTHER PUBLICATIONS

Brochure for "The CALM System: the computer assisted labor monitoring system," LMS Medical Systems Limited, Montreal, Quebec, Canada (Spring 1998).

Emily Hamilton et al., "Computerized Assessment of Labor in Women with Intrapartum Uterine Rupture," Obstetrics & Gynecology, Abstracts of Papers and Posters to be Presented at the ACOG 47th Annual Clinical Meeting, Philadelphia, PA (May 15–19, 1999).

(List continued on next page.)

*Primary Examiner*—Kevin Shaver
*Assistant Examiner*—Brian Szmal
(74) *Attorney, Agent, or Firm*—Ratner & Prestia

(57) ABSTRACT

An apparatus for tracking the labor progress of a patient during childbirth. Clinical measurements associated with a patient are received including a measurement of a previous dilatation of the cervix, a contraction count, a previous level of descent of the child, a previous effacement measurement of the cervix, an epidural status, and a parity status. The clinical measurements are processed to generate an expected future dilatation of the cervix by taking a linear combination of the clinical measurements. The expected dilatation of the cervix can then be used to assist a physician in determining whether a cesarean delivery is appropriate. A system for tracking labor progress is provided including a broker unit, a labor progress unit, and an information-gathering unit. The broker unit coordinates the communications in the system by receiving messages and forwarding messages to the components of the system as well as by providing publish/subscribe capabilities.

52 Claims, 7 Drawing Sheets

U.S. PATENT DOCUMENTS

Emily Hamilton et al., "Intrapartum Prediction of Fetal Status and Assessment of Labour Progress," Bailliere's Clinical Obstetrics and Gynaecology, pp. 567–581 (1994).
Examples of Hospital Printouts (Spring 1998).
Eric Gamma et al., "Design Patterns, Elements for Resuable Object Oriented Software," pp. 99–121 (1995).
Clinical Trial Site Agreement (Mar. 10, 1999).
Exhibit D: Clinical Trial Agreement (Mar. 10, 1999).
Communication Relating to the Results of the Partial International Search (Annex to Invitation to Pay Additional Fees) (Dated Nov. 15, 2001.

Hamilton et al., "Dystocia Among Women with Symptomatic Uterine Rupture," Americal Journal of Obstetrics and Gynecology, vol. 184, No. 4, pp. 620–624 (Mar. 2001).

Hamilton et al., "An Application of Real Time Decision Support in Obstetrics," Proc. of the Intern. Conf. of Neural Networks and Expert Systems in Medicine and Healthcare, Plymouth, UK, pp. 446–455 (Aug. 23–26, 1994).

Hamilton et al., "A Comprehensive Labor Surveillance System," Journal of Perinatal Medicine, vol. 15, No. Suppl. 1, p. 144 (1987).

International Search Report dated Mar. 8, 2002.

SYSTEM AND METHOD FOR EVALUATING LABOR PROGRESS DURING CHILDBIRTH

FIELD OF THE INVENTION

This invention relates to the field of medical diagnostic devices and systems in the area of clinical obstetrics and more particularly to a system and method for the assessment of labour progress during childbirth. This invention is applicable in assisting decision making in clinical medicine and can be used to reduce the number of unnecessary caesarean deliveries.

BACKGROUND OF THE INVENTION

The labor of childbirth is the process by which uterine contractions cause the fetus and placenta to be expelled from the uterus and birth canal. Rhythmic contractions of the uterine muscle create a force that pushes the fetus against the opening of the uterus, commonly referred to as the cervix. The cervix is a tubular structure that is firm and closed during pregnancy, keeping the baby and membranes protected inside the uterus. At term, the cervix softens and in labor the continuing pressure of the fetus on the cervix causes it to shorten (efface) and to open (dilate) up to 10 centimeters. As the cervix completely effaces and dilates, the contractions and the mother push the baby through the birth canal. The level of descent of the baby through this passage is referred to as station. Contractions are the forces that promote cervical dilatation. Resistance of the cervix and the birth canal are the opposing forces to the contractions. In addition, the resistance of the cervix changes as it becomes more effaced and more dilated.

Commonly, the effacement, the dilatation, the frequency of the contractions and the station are measured clinically during labor and are used by the doctors to determine if the labor is progressing normally. Generally, if the doctor determines that the labor is progressing normally, the delivery is permitted to continue through the birth canal. However, if the doctor determines that the labor is not progressing normally, a cesarean section is effected to complete the delivery.

Cesarean deliveries are associated with maternal morbidity and an increase in the risk of complications during the current and the subsequent pregnancies. Cesarean deliveries are also more expensive than vaginal births.

Due to the very large number of possible combinations of values for the dilation, the effacement, the frequency of the contractions and the station, the evaluation of labor progress is a difficult task for doctors. Unlike most surgical procedures, there is no suitable postoperative confirmation of the preoperative diagnosis that can be used to validate the doctor's decision. By examining outcomes and cesarean rates in various centers, it is likely that a large number of cesarean deliveries may have been unnecessary.

Consequently, there is a need in the industry for providing an improved system and method for evaluating labor progress during childbirth such as to reduce the number of unnecessary cesarean deliveries.

SUMMARY OF THE INVENTION

In accordance with a broad aspect, the invention provides a method and apparatus for tracking the labor progress of a patient during childbirth. The apparatus includes an input for receiving a group of clinical measurements associated to a patient. The group of clinical measurements include clinical measurement collection during the last pelvic exam. The group of clinical measurements includes data elements indicative of a measurement of a previous dilatation of the cervix of the patient, a contraction count, a previous level of descent of the child, a previous effacement measurement of the cervix, an epidural status and a parity status. The parity status is indicative of either one of a first childbirth for the patient and a childbirth subsequent to a first childbirth. The apparatus also includes a processing unit operative for generating a reference measure indicative of a certain expected dilatation of the cervix allowing to assess the progress of childbirth by using the following formula:

$$x = AA + BB*(1-y) + CC*z + DD*w + EE*v + FF*u$$

where:
- $x$ is the certain expected dilatation of the cervix;
- $y$ is the epidural status;
- $z$ is the previous dilatation of the cervix measurement;
- $w$ is the previous effacement measurement of the cervix;
- $v$ is the previous level of descent of the child;
- $u$ is the contraction count;

and where $AA$, $BB$, $CC$, $DD$, $EE$ and $FF$ are a set of real numbers conditioned at least in part on the basis of the parity status. A signal indicative of a measurement of the certain expected dilatation of the cervix is released at an output.

In accordance with a specific example of implementation, the formula includes an error estimate data element indicative of a residual value. The processing unit is further operative to derive a range of expected dilatations of the cervix having a normal distribution on the basis of the error estimate.

Continuing the specific example of implementation, the group of clinical measurements includes a data element indicative of a current dilatation of the cervix measurement. The current dilatation of the cervix measurement to derive a ranking data element indicative of a percentile ranking of the current dilation of the cervix measurement with respect to the range of expected dilatations of the cervix on the basis of the certain expected dilatation of the cervix and the error estimate. A signal indicative of the ranking data element is then released at the output.

In accordance with a broad aspect, the invention provides the use of the signal indicative of the ranking data element released by the apparatus described here above for assisting in the determination of whether a cesarean delivery is required for the patient. More specifically, the ranking data element is indicative of the performance of the patient with respect to a reference population. For instance, a percentile of 90 means that the performance of this patient is at the level of, or is better than the lowest 90 out of 100 similar patients who delivered vaginally. In other words, this performance is much faster than average. A percentile ranking of 10 means that the performance of this patient is at the level of, or is better than the lowest 10 out of 100 similar patients who delivered vaginally. In other words, this performance is much slower than average. If a patient has a performance below a certain percentile, herein designated as the minimum normal percentile, the doctor may make the decision that a cesarean may be recommended. The minimum normal percentile may be determined by the hospital in which the delivery is taking place or by health standards or the likes. Typical minimum normal percentiles are in the range of 1.5 to 4 but may be higher or lower depending upon the hospital (or health institution policies) and depending on the condition of the patient.

An advantage of the present invention is that abnormal labor patterns can be more objectively diagnosed thereby potentially reducing the number of unnecessary cesarean deliveries.

In accordance with another broad aspect, the invention provides a computer readable medium comprising a program element suitable for execution by a computing apparatus for implementing the above-described apparatus.

In accordance with another broad aspect, the invention provides a system for tracking the labor progress of a patient during childbirth. The system includes an information gathering unit associated to a first entity identifier, the information gathering unit being suitable for receiving a group of clinical measurements associated to a patient. The system also includes a labor progress unit associated to a second entity identifier. The labor progress unit is operative for generating a reference measure indicative of a certain expected dilatation of the cervix allowing to assess the progress of childbirth. The system also includes a broker unit comprising a first communication port suitable for exchanging messages with the information gathering unit, each message including a destination entity identifier. The broker unit also comprises a second communication port suitable for exchanging messages with the labor progress unit, each message including a destination entity identifier. The broker unit also comprises a processor operative for processing a certain message received from the information gathering unit at the first communication port such as to forward it to the second communication port for transmission to the labor progress unit when the certain message includes a destination entity identifier matching the second entity identifier.

In accordance with a specific example, the processor of the broker unit is further operative for processing a certain message received from the labor progress unit at the second communication port. The processing unit forwards the message to the first communication port for transmission to the information gathering unit when the certain message includes a destination entity identifier matching the first entity identifier.

In accordance with another specific example, the system comprises a set of information gathering units, each information gathering unit of said set of information gathering unit being associated with a respective first entity identifier. The first communication port of the broker unit is suitable for exchanging messages with each information gathering unit of the set of information gathering units.

Continuing the specific example of implementation, the broker unit further comprises a data structure including a plurality of entries, at least one entry being associated to the labor progress unit. The entry includes a subscriber list suitable for storing at least one first entity identifier associated to a certain information gathering unit from the set of information gathering units. The processor of the broker unit is further operative for processing a certain message received from the labor progress unit at the second communication port such as to forward it to the first communication port for transmission to the certain information gathering unit associated to the first entity identifier in the subscriber list.

Other aspects and features of the present invention will become apparent to those ordinarily skilled in the art upon review of the following description of specific embodiments of the invention in conjunction with the accompanying figures.

DETAILED DESCRIPTION

Figure 1:
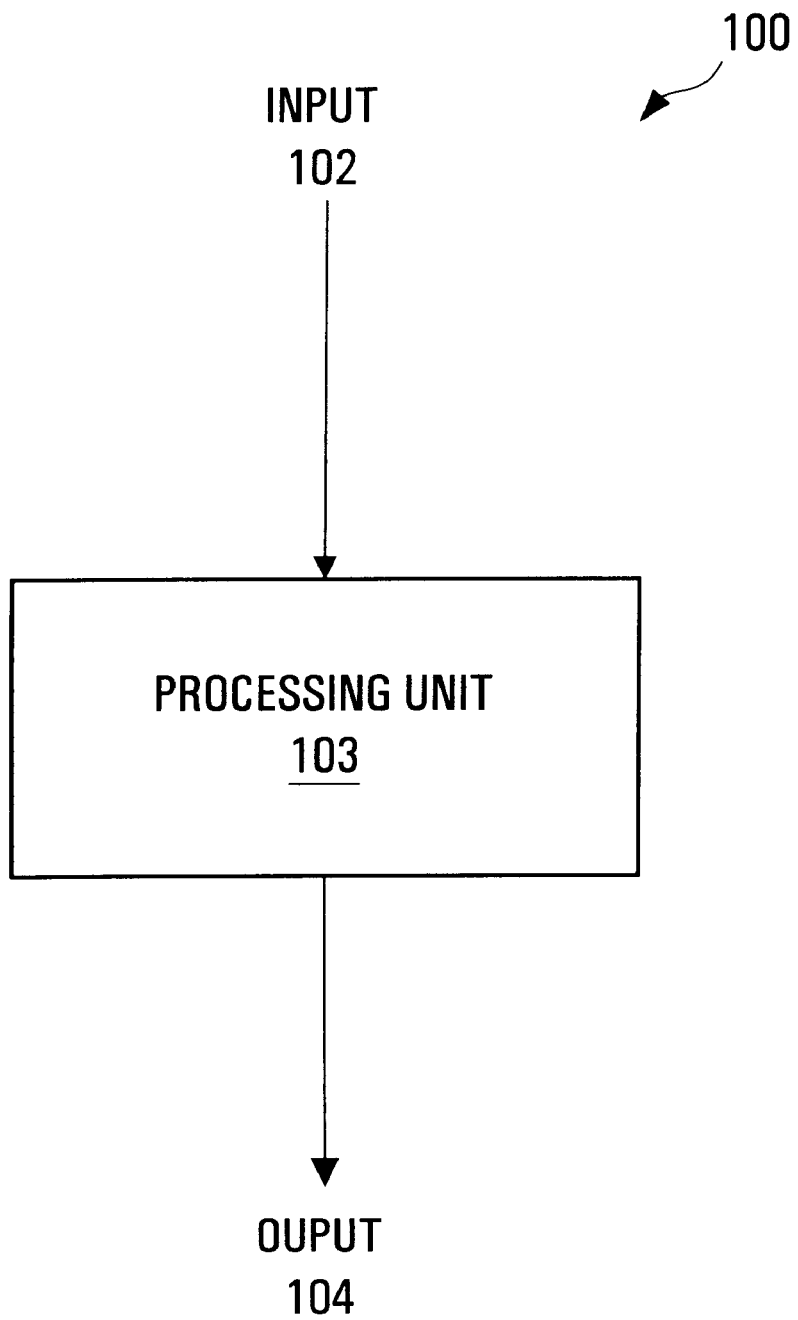
FIG. 1 is a block diagram of an apparatus for tracking the labor progress of a patient during childbirth in accordance with a specific example of implementation of the present invention.

In a specific example of implementation, as shown in FIG. 1, the invention provides an apparatus 100 for tracking the labor progress of a patient during childbirth. The apparatus 100 includes an input 102, a processing unit 103 and an output 104.

The input 102 is for receiving a group of clinical measurements associated to a patient. The group of clinical measurements includes measurements taken during the last pelvic exam. These measurements will be used to calculate an expected value of the dilatation of the cervix. The group of clinical measurements includes data elements indicative of a measurement of a previous dilatation of the cervix of the patient, a contraction count, a previous level of descent of the child (station), a previous effacement measurement of the cervix, an epidural status and a parity status. More specifically, the clinical measurements are expressed as follows:

Epidural status =0 if none, =1 if present previous dilatation of the cervix measurement=dilatation of the cervix at the previous pelvic examination in centimeters previous effacement measurement of the cervix=previous effacement in percent/10 previous level of descent of the child=level of descent of the child as recorded clinically (−3 to +3) at the previous examination converted to a positive linear scale from 0 to 7. In other words, if the previous level of descent of the child is 1, then the value to be used is 4 (1+3).

Contraction count is the cumulative contraction count from the time the labor monitoring was started an the first pelvic exam was done. In a specific non-limiting example, contractions are detected algorithmically from a fetal monitor recording and the contraction count is a count of contractions from the time the electronic fetal monitor is applied.

The parity status is indicative of either one of a first childbirth for the patient and childbirth subsequent to a first childbirth. In a non-limiting example, the parity status can take on either one or two values namely a "0" if it is a first childbirth and "1" for other cases. A data element indicative of a current dilatation of the cervix measurement is also received at the input 102.

The output 104 is for releasing a signal indicative of a certain expected dilatation of the cervix. In a specific example of implementation, the output also releases a signal indicative of a band of expected dilatations of the cervix. The expected dilatation of the cervix and the band of expected dilatations are calculated by the processing unit 103 at time intervals on the basis of a sequence of groups of clinical measurements received at the input 102 at these time intervals such as to provide a historical evolution of the patient performance during labor. The result of these calculations is a sequence of expected dilatations of the cervix and bands of expected dilatations of the cervix associated to a sequence of time intervals. The signal indicative of a graphical representation of the sequence of expected dilatations of the cervix and the bands of expected dilatations are released at the output 104. In a very specific example, a curve corresponding to the sequence of expected dilatations of the cervix and ranges of expected dilatations is released at the output 104. The output 104 also releases a signal indicative of a ranking data element. The ranking data element is indicative of a percentile ranking of the current dilatation of the cervix with respect to the calculated certain expected dilatation of the cervix.

In a specific example of implementation, a graphical display unit is coupled to the output 104 such as to provide a visual display of the results. Very specific examples of graphical display units include a computer monitor, a TV monitor, a LCD screen, and a printer among many other suitable display devices.

Figure 3:
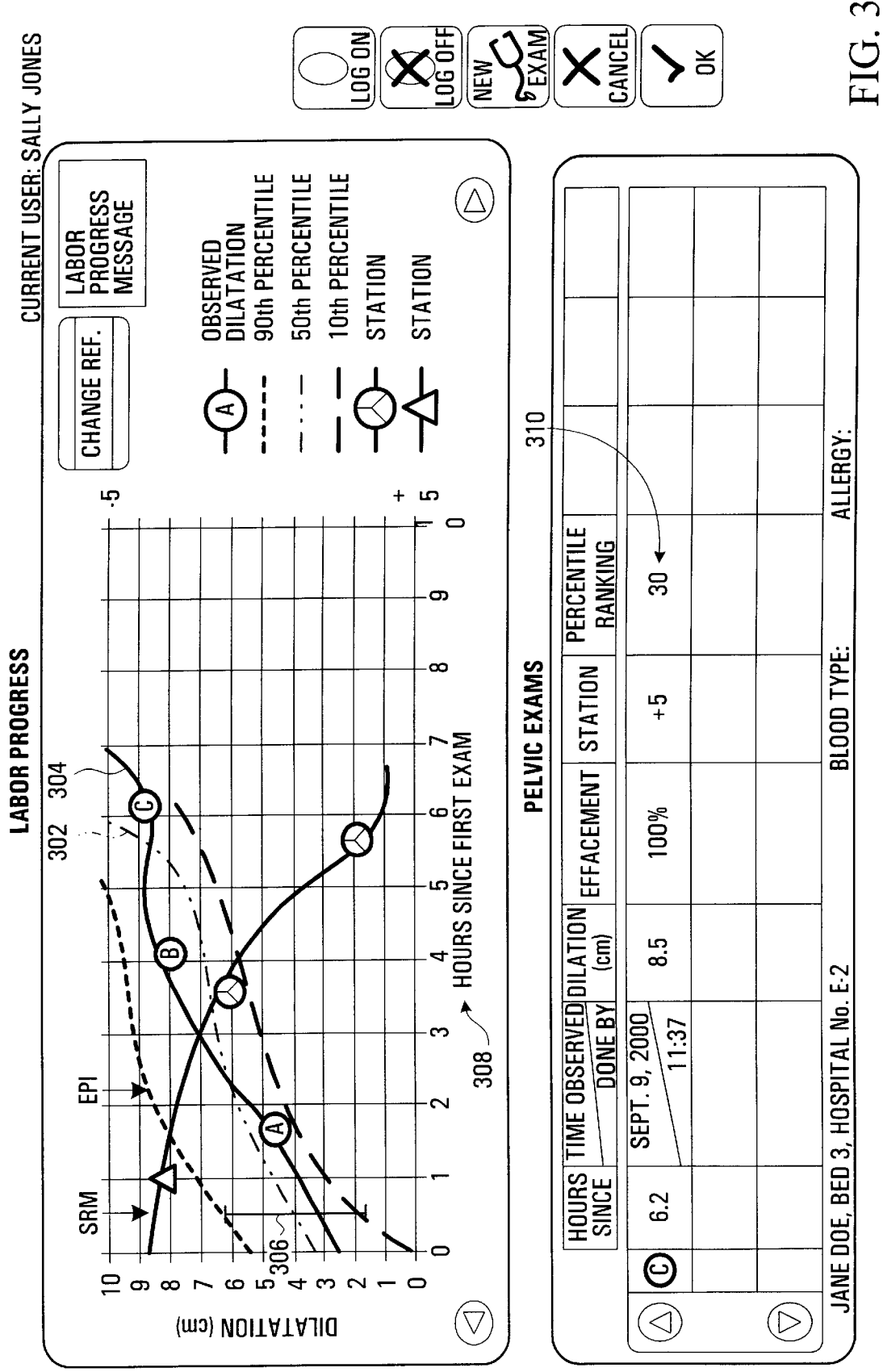
FIG. 3 is a specific example of a graphical representation of the output signal released by the apparatus of FIG. 1.

FIG. 3 shows a specific example of a graphical representation 350 of the expected dilatation of the cervix 302, the actual dilatation of the cervix 304 and the band of expected dilatations of the cervix 306 as plotted with respect to time 308. The current percentile ranking 310 is also shown.

The processing unit 103 is coupled to the input 102 and the output 104. The processing unit is operative for generating a reference measure indicative of a certain expected dilatation of the cervix allowing assessing the progress of childbirth. A range of expected dilatations of the cervix having a normal distribution is also computed on the basis of an error estimate as well as a ranking data element indicative of a percentile ranking of the current dilatation of the cervix with respect to the calculated expected dilatation. In particular, the ranking data element is released by the apparatus and is used by a doctor for evaluating the progress of labor including assisting in the determination of whether a cesarean delivery is required for the patient.

Figure 2:
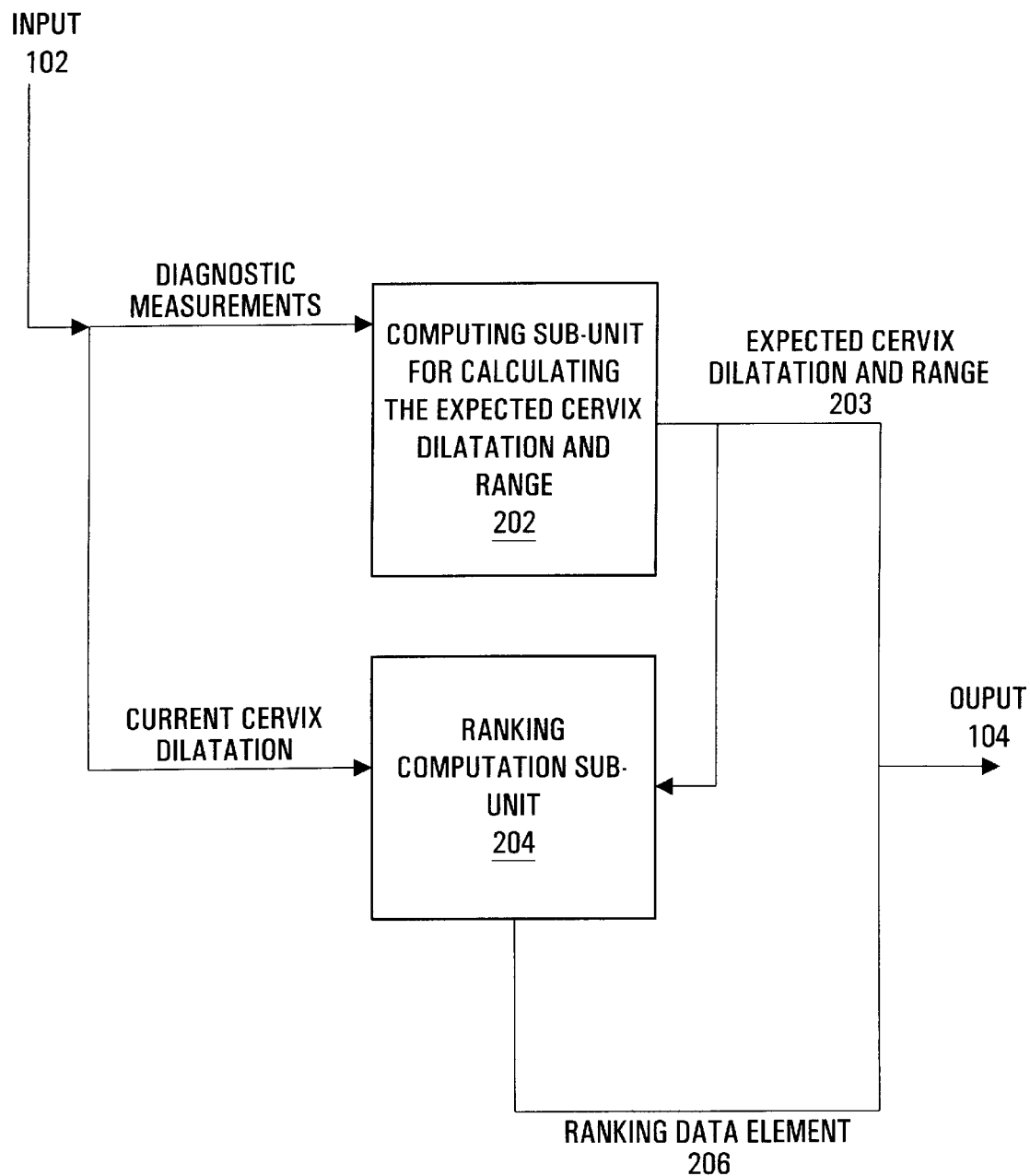
FIG. 2 is a functional block diagram of the processing unit depicted in FIG. 1.

The functionality of the processing unit 103 will be best understood in connection with FIG. 2 of the drawings. The processing unit can be divided into two sub-units namely a computing sub-unit 202 for calculating the expected cervix dilatation and range of expected cervix dilatations at a certain time and a ranking computation sub-unit 204.

The computing sub-unit 202 generates a reference measure indicative of a certain expected dilatation of the cervix and a range of expected dilatations of the cervix. The computing sub-unit 202 receives as an input the group of clinical measurements namely the previous dilatation of the cervix of the patient, the contraction count, the previous level of descent of the child, the previous effacement measurement of the cervix, the epidural status and the parity status. The group of clinical measurements is processed to compute an expected cervix dilatation and a range of expected cervix dilatations. The computing sub-unit 202 then releases at an output 203 an expected cervix dilatation.

Mathematically, the calculation of the expected dilatation measurement can be expressed by a formula having the form:

$$x = AA + BB^*(1-y) + CC^*z + DD^*w + EE^*v + FF^*u \qquad \text{Equation 1}$$

where x is the certain expected dilatation of the cervix; y is the epidural status; z is the previous dilatation of the cervix measurement; w is the previous effacement measurement of the cervix; v is the previous level of descent of the child; u is the contraction count; and where AA, BB, CC, DD, EE and FF are a set of real numbers conditioned at least in part on the basis of the parity status.

In accordance with a specific example of implementation, equation 1 includes an error estimate data element indicative of a residual value The error estimate defines a range of expected dilatations of the cervix having a normal distribute about the certain expected dilation of the cervix (which is the mean of the normal distribution).

The error estimate allows calculating a band of expected dilatations of the cervix, the band being defined by a lower boundary and an upper boundary. In a specific example, the band of expected dilatations of the cervix is derived by providing deviation values from the certain expected dilatation of the cervix thereby allowing a band of expected dilatations of the cervix to be defined. Mathematically, the band of expected dilatations of the cervix can be expressed as follows:

$$\text{Band} = [x - z_1 R; \ x + z_2 R] \qquad \text{Equation 2}$$

where x is the certain expected dilatation of the cervix; R is the error estimate and $z_1$ (lower deviation) and $z_2$ (upper deviation) are selected on the basis of a desired area under a curve indicative of the normal distribution of the expected dilations of the cervix. The person skilled in the art will readily observe that the upper deviation and lower deviation may differ from one another without detracting from the spirit of the invention. For the purpose of simplicity, it will be assumed that the lower deviation and the upper deviation have the same value and the expression boundary deviation will be used to designate both the lower deviation and the upper deviation. In a specific example, the boundary deviation is a real number.

In a non-limiting example, the computing sub-unit 202 provides two sets of real numbers AA, BB, CC, DD, EE and FF, namely a first set and a second set, each set being associated to a respective parity status. The computing sub-unit 202 processes the parity status data element to select a set of real numbers on the basis of the parity status. In other words, the expected dilatation measurement of a cervix during childbirth is dependent at least in part upon whether the childbirth is a first childbirth (primiparous women) for the patient or a childbirth subsequent to a first childbirth (multiparous women). In addition, the computing sub-unit 202 also provides two error estimate values, namely a first error estimate and a second error estimate, each error estimate being associated to a respective parity status.

More specifically, when the parity status is indicative of a first childbirth, the error estimate has a value of about 1.3 and the set of real numbers is a first set characterized by:

i. AA having a value of about 2.5;

ii. BB having a value of about 0.15;

iii. CC having a value of about 0.8;

iv. DD having a value of about 0.24;

v. EE having a value of about 0.04;

vi. FF having a value of about 0.004.

A very specific non-limiting example of implementation makes use of a error estimate of 1.3014 and a first set characterized by:

i. AA having a value of about 0.24952;
ii. BB having a value of about 0.14627;
iii. CC having a value of about 0.80515;
iv. DD having a value of about 0.24109;
v. EE having a value of about 0.03909;
vi. FF having a value of about 0.00447.

Continuing the specific example of implementation, when the parity status is indicative of a childbirth subsequent to a first childbirth, the error estimate has a value of about 1.3 and the set of real numbers is a second set characterized by:

i. AA having a value of about 2;
ii. BB having a value of about 0.2;
iii. CC having a value of about 0.8;
iv. DD having a value of about 0.15;
v. EE having a value of about 0.2;
vi. FF having a value of about 0.01.

A very specific non-limiting example of implementation makes use of a error estimate of 1.3451 and a second set characterized by:

i. AA having a value of about 1.9914;
ii. BB having a value of about 0.23484;
iii. CC having a value of about 0.7770;
iv. DD having a value of about 0.15503;
v. EE having a value of about 0.20669;
vi. FF having a value of about 0.00766.

The skilled person in the art will readily appreciate that the above coefficient values depend on the units used with respect to the clinical measurements and that conversion values may be applied to the above real numbers to adapt the equation to measuring units different from the ones used in this specific example. For instance, in the examples presented in this description, the previous dilatation of the cervix measurement is measured in centimeters (cm) and therefore the coefficient CC is conditioned on that basis. In order to use a previous dilatation of the cervix measurement measured in inches, the appropriate conversion factor must be applied to the coefficient CC. The same principle applies to the other coefficients.

The expected cervix dilatation can be compared to the to the actual or observed dilatation in order to determine if the labor is progressing normally or whether a cesarean delivery is required.

The ranking computation sub-unit 204 is coupled to the output of the computing sub-unit 202 and receives as input the expected cervix dilatation and the error estimate computed by the computing unit 202. The ranking computation sub-unit 204 also receives as input a measure of the current dilation of the cervix. The measure of the current dilatation of the cervix is processed by the ranking computation sub-unit 204 to derive a ranking data element indicative of a percentile ranking of the current dilatation of the cervix with respect to the error estimate and the certain expected dilation of the cervix. The ranking data element is then released at an output 206.

Advantageously, the error estimate and the certain expected dilatation of the cervix defined a range of expected dilatations having a normal distribution thereby allowing the difference between the actual and the expected dilations to be expressed in percentiles. In a specific example of implementation, the percentile ranking is computed on the basis of the assumption that the range of expected dilatations of the cervix is indicative of a normal distribution (bell shaped). Statistical methods can be used to compute the percentile ranking and are well known in the art to which this invention pertains and will not be further described here. As an example, a percentile can be calculated by the following formula:

$$\text{Percentile} = \int (n) * [(\text{current\_x} - x)/R]$$

Where n is the normal distribution and current_x is the current dilatation measurement of the cervix.

Advantageously, the percentile ranking can be used by a doctor to assess the labor progress of the patient with respect to a reference population. The usual fashion of interpreting percentile rankings can be used. For instance, a percentile of 90 means than the performance of the patient is at the level of, or is better than the lowest 90 out of 100 similar patients who delivered vaginally. In other words, this performance is much faster than average. A percentile ranking of 10 means that the performance of the patient is at the level of, or is better than the lowest 10 of 100 similar patients who delivered vaginally. In other words, this performance is much slower than average. The percentile ranking can be used in assisting the doctor to determine whether a cesarean delivery is recommended. For instance, if a patient has a performance below the minimum normal percentile, the doctor may take the decision that a cesarean is to be recommended. The minimum normal percentile may be determined by the hospital in which the delivery is taking place or by health standards or the likes. Typical minimum normal percentiles are in the range of 1.5 to 4 but may be higher or lower depending upon the hospital (or health institution policies).

Figure 4:
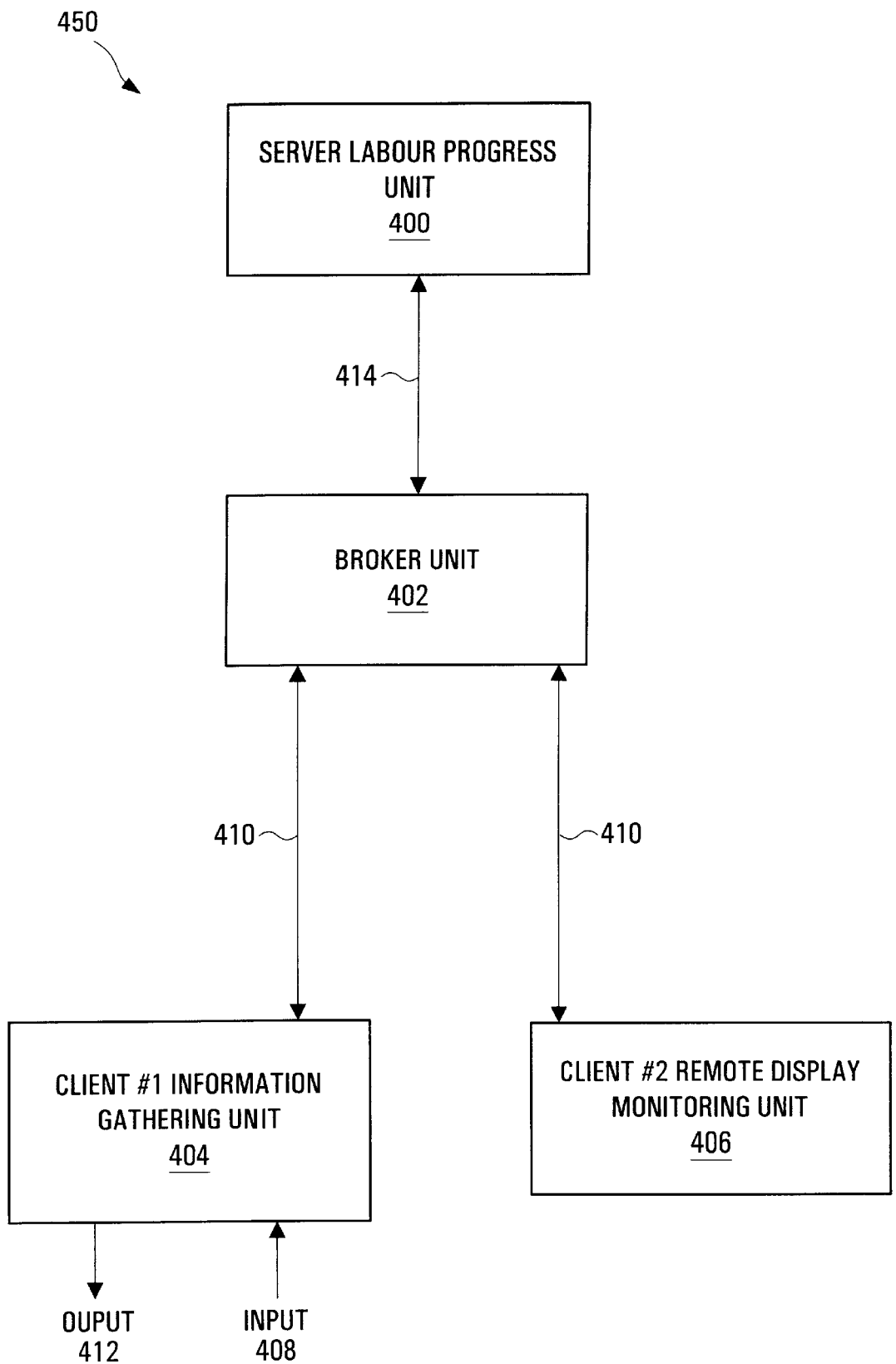
FIG. 4 is a block diagram of a system including a broker unit for tracking the labor progress of a patient during childbirth in accordance with an alternative example of implementation of the present invention.

In a second form of implementation, as shown in FIG. 4, the invention provides a system 450 for tracking the labor progress of a patient during childbirth. In a specific example of implementation, the system makes use of a broker unit network architectural pattern. The system includes a set of components namely server units, a broker unit 402 and a set of client units. A plurality of server units and any number of client units may be present in the system 450 without detracting from the spirit of the invention. For the sake of simplicity, a system including a single server unit namely the labor progress unit 400 and two client units namely an information gathering unit 404 and a remote display monitoring unit 406 will be described herein below.

In the broker unit network architectural pattern, the components of the network are co-ordinated by the broker unit 402. Each component in the set of components is associated to a respective entity identifier allowing distinguishing a certain component from the other components in the set of components. Components communicate with one another using the entity identifiers in combination with well-known communication protocols such as for example the Transmission Control Protocol/Internet Protocol (TCP/IP).

Figure 5:
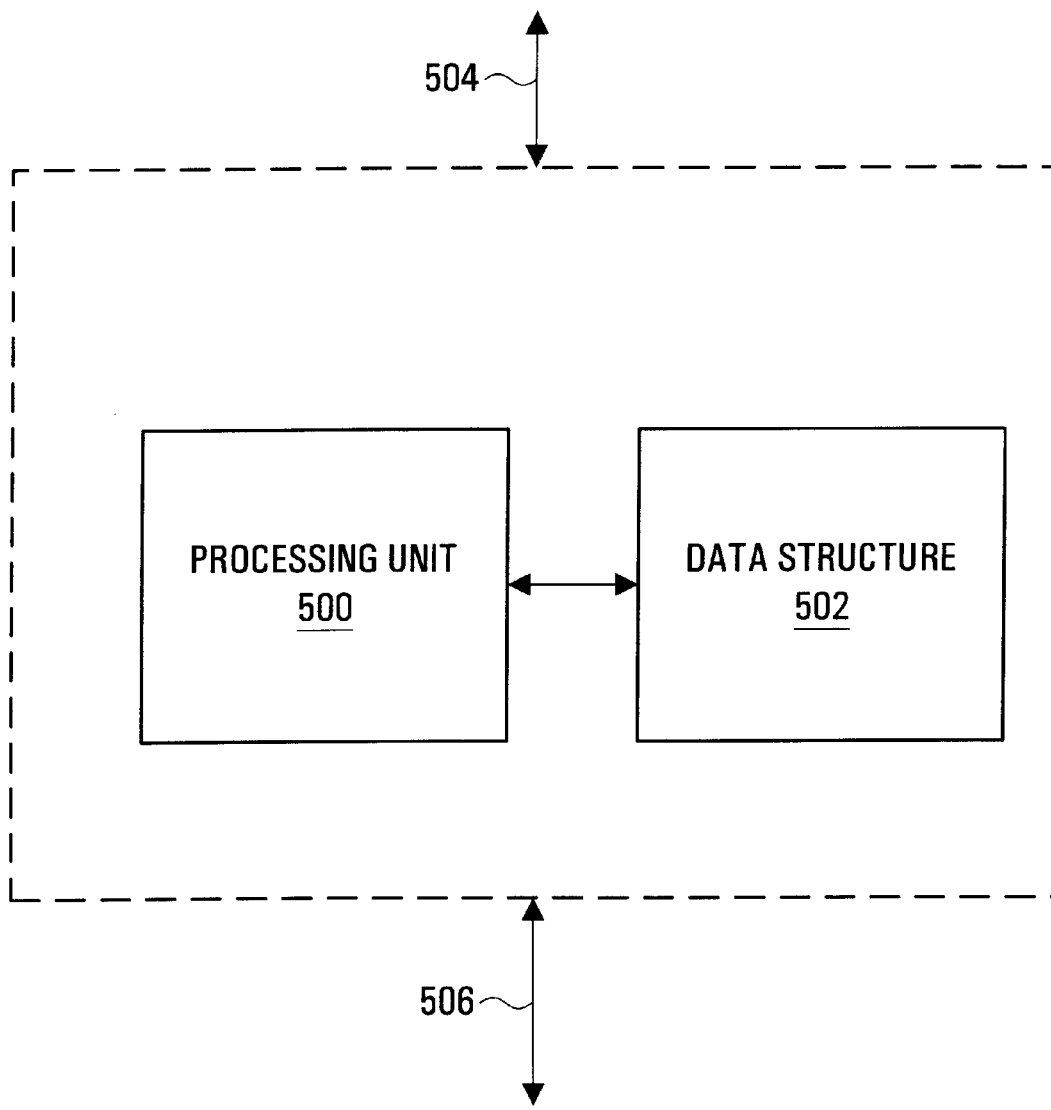
FIG. 5 is a functional block diagram of the broker unit depicted in FIG. 4 in accordance with a specific example of implementation of the present invention.

In a specific example of implementation, as shown in FIG. 5, the broker unit 402 comprises a first communication port 506 suitable for exchanging data with the information gathering unit 404 and a second communication port 504 suitable for exchanging data with the labor progress unit 400. In accordance with the specific example of implementation, the system 450 makes use of a message passing broker pattern. The broker unit 402, the labor progress unit 400, the information gathering unit 404 and the remote display monitoring unit 406 communicate by sending and receiving messages. Each message is a data structure including a destination entity identifier, a sender entity identifier and data elements. This may be implemented by using well know software components such as for example Microsoft™ Message Queue Server. The skilled person in the art will readily appreciate that broker patterns making use of communication data structures other than messages may be used here without detracting from the spirit of the invention.

The broker unit 402 also includes a data structure 502 including a plurality of entries. Each entry is associated to a respective component of the system and allows the broker unit to locate the components within the system. More specifically, each entry in the data structure includes the entity identifier of the component along with an address data element. For example, the entity identifier may be associated to an IP address, a process number or any other suitable way of locating a component in the system. The data structure is such that by searching and locating an entity identifier, the address data element can be extracted.

More specifically, for each component in the system 450, an entry is created in the data structure of the broker unit 402. Continuing the specific example of implementation, at least one entry in the data structure is associated to the following components:

the labor progress unit 400;
the information gathering unit 404;
the remote display monitoring unit 406.

The broker unit 402 also includes a processing unit 500 operative for processing a certain message received from the information gathering unit 404 at the first communication port 506 to extract therefrom a destination entity identifier. The broker unit then locates in the data structure 502 the destination entity identifier and extracts therefrom the address data element associated with the destination entity identifier. The message is then forwarded to the second communication port 504 for transmission to the destination components corresponding to the destination entity identifier on the basis of the extracted address. The processor of the broker unit 402 is also operative for processing a certain message received from the labor progress unit at the second communication port 504. The message is processed to extract therefrom a destination entity identifier. The broker unit then locates in the data structure 502 the destination entity identifier and extracts therefrom the address data element associated with the destination entity identifier. The message is then forwarded to the first communication port 506 for transmission to the information gathering unit when the certain message includes a destination entity identifier matching the entity identifier corresponding to the information gathering unit.

As a variant, the broker unit 402 further provides publishing/subscribing capabilities. In a specific example, the broker unit makes use of a publish/subscribe pattern (also known as the Observer pattern) which is well known in the art of networks. In this pattern, components in the system can subscribe to events. When these events occur, subscribers to the event are notified. Advantageously, making use of a publish/subscriber pattern instead of other information sharing patterns such as polling allows a reduction in the network bandwidth and resources required.

More specifically in this variant, the entry in the data structure 502 of the broker unit associated to servers, such as the labor progress unit 400, includes a link to a subscriber list suitable for storing entity identifiers. The processor of the broker unit is operative for processing a certain message received from the labor progress unit at the second communication port such as to forward it to each component having an entity identifier in the subscriber list. In this fashion, the component of the system desirous of obtaining information about the result of the labor progress unit automatically receives updates without the requirement to poll the labor progress unit. For example, a centralized nursing station may have a device for displaying showing the labor progress of a patient (or several patients) in various rooms in the obstetrics department. This is shown as the remote display monitoring unit 406 in FIG. 4.

For more information regarding the use of broker units and publish/subscribe functionality, the reader is invited to consult "Design Patterns, Elements of Reusable Object-oriented Software", Erich Gamma et al., Addison-Wesley, 1995 whose content is hereby incorporated by reference.

The set of client units 404 406 includes components such as computer terminals, display units and printers among others. Each client unit is associated to a respective entity identifier allowing distinguishing a certain client unit from the other client units in the set of client units. Each client unit 404 406 includes in input/output port 410 (I/O) for communicating with the broker unit 402.

In a specific example of implementation, the set of client units 404 406 includes an information gathering unit 404 associated to a first entity identifier. The information-gathering unit has an input 408 suitable for receiving a group of clinical measurements associated to a patient. The group of clinical measurements is essentially similar to that described in connection with the input 102 shown in connection with the apparatus of FIG. 1. Consequently all the characteristics and variants described for the group of clinical measurements apply here as well and will therefore not be described further. The input 408 of the information gathering unit may be in the form of a keyboard, a pointing device such as a mouse coupled to a monitor, a microphone coupled to a speech recognition device, a fetal monitor unit or any other type of input device suitable for receiving data elements indicative of clinical measurements.

The information-gathering unit 404 also includes an output 412 suitable for releasing a signal indicative of a graphical representation of a certain expected dilatation of the cervix. In a specific example of implementation, the output 412 also releases a signal indicative of a graphical representation of a band of expected dilatations of the cervix. The output 412 also releases a signal indicative of a ranking data element. The ranking data element is indicative of a percentile ranking of the current dilatation of the cervix with respect to the calculated certain expected dilatation of the cervix. The output signal is suitable to be displayed by a graphical display unit. In a specific example of implementation, a graphical display unit is coupled to the output 412 such as to provide a graphical display of the results. Very specific examples of graphical display units include a computer monitor, a TV monitor, a LCD screen, and a printer among many other suitable display devices. The output signal released by the output 412 is essentially similar to that described in connection with the output 104 shown in connection with the apparatus of FIG. 1. Consequently all the characteristics and variants described for the output signal apply here as well and will therefore not be described further.

The information gathering unit 404 also includes a processor operative for assembling the group of clinical measurements into a message data structure for transmission to the broker unit 402. The message data structure includes a destination entity identifier, the first entity identifier associated to the information gathering unit 404 and the group of clinical measurements among others. Messages are a well-known communication device used in distributed computer networks and thus will not be described in further detail here.

The labor progress unit 400 is associated to a second entity identifier allowing distinguishing the labor progress unit from other server units and the client units in the system. The labor progress unit 400 includes an input/output port 414 (I/O) for communicating with the broker unit 402. The labor progress unit is operative for generating a reference measure allowing to assess the progress of childbirth. The labor progress unit 400 implements essentially the same functionality as the processing unit 103 described in connection with FIG. 1 of the drawings. The labor progress unit 400 is further adapted to receive a message from the broker unit 402 and extract therefrom data element indicative of a group of clinical data elements prior to processing. The labor progress unit 400 is also adapted to assemble the results of the processing into a message data structure for transmission to the broker unit 402. The message data structure includes among others a destination entity identifier, the second entity identifier associated to the labor progress unit 400 and the results of the processing. Messages are a well-known communication device used in distributed computer networks and thus will not be described in further detail here.

Figure 6:
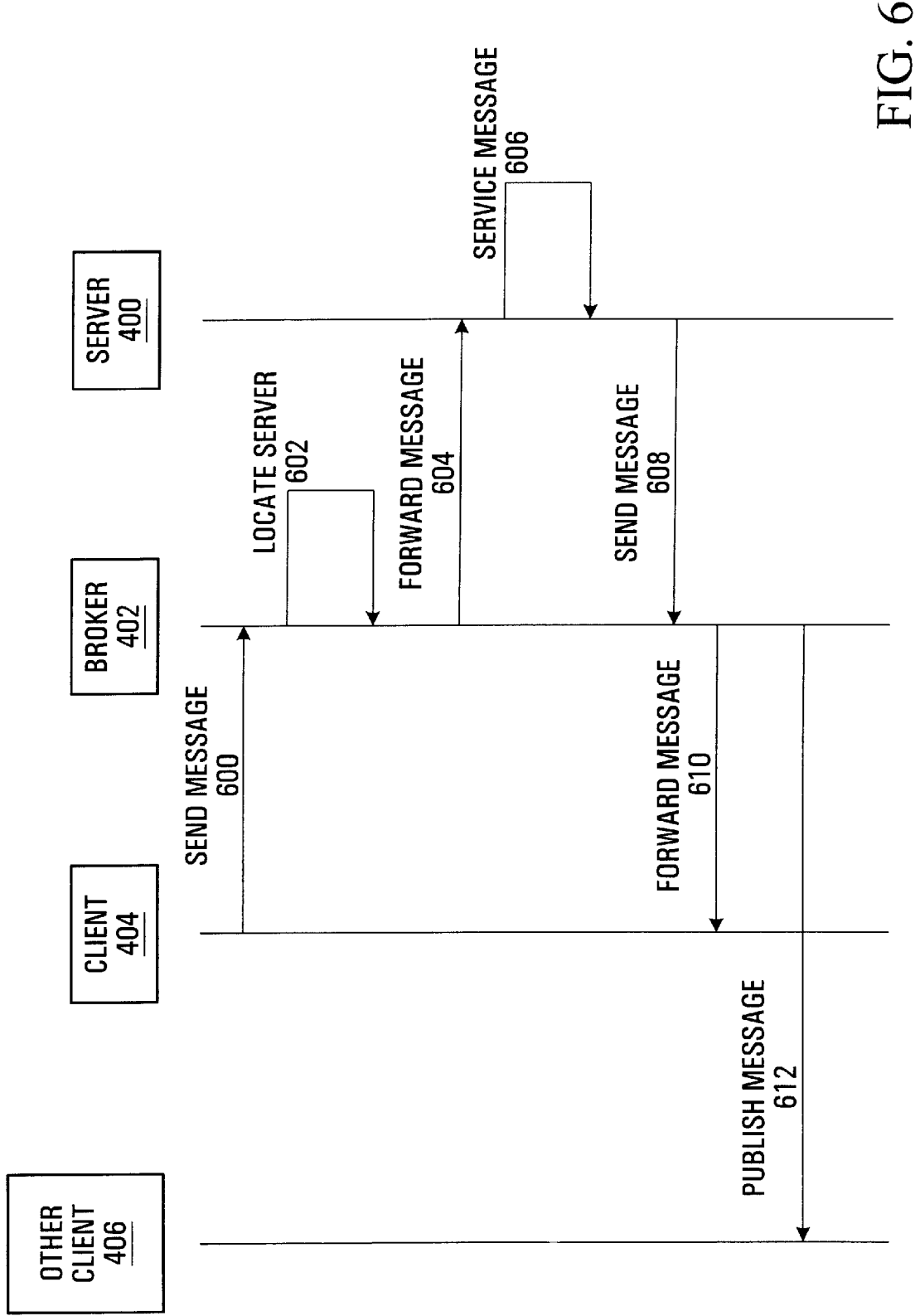
FIG. 6 is a flow diagram of a process for tracking the labor progress of a patient during childbirth implemented by the system depicted in FIG. 4.

A typical interaction will better illustrate the process implemented by the system 450. In this interaction, the components 400, 404 and 406 have already provided their addresses to the broker unit, and the remote display monitoring unit 406 has subscribed to the labor progress unit 400 and is therefore in the subscriber list associated to the broker data structure entry corresponding to the labor progress unit 400. As shown in FIG. 6, the information gathering unit 404 sends a message 600 to the broker unit including a group of clinical measurements, a destination entity identifier, a sender entity identifier and requesting the services of the labor progress module 400. The broker unit 402 processes the message and locates the data structure entry corresponding to the destination entity identifier. Once the labor progress unit 400 has been located 602, the message is forwarded at step 604 to the labor progress unit 400. At step 606, the labor progress unit 400 performs its computations and generates a message containing the results. The message has a destination entity identifier corresponding to the information gathering unit 404. At step 608, the message is sent from the labor progress unit 400 to the broker unit. The broker unit 402 processes the message and locates the data structure entry corresponding to the destination entity identifier. Once the information gathering unit 404 has been located, the message is forwarded at step 610 to the information gathering unit 404. Following this, the broker unit also locates in the data structure the entry corresponding to the labor progress unit 400 and processes the subscriber list to which it is associated. In this example, the subscriber list includes an entity identifier associated to the remote display monitoring unit 406. The broker unit forwards the message received from the labor progress module to the remote display monitoring unit 406 at step 612.

Advantageously, by making use of a broker unit network architectural pattern for the system 450, an increased scalability of the system can be obtained. For example, the system 450 may be extended by adding client units, server units without the need to modify or update the existing components.

Another advantage of this type of architecture is location transparency. Since the broker unit locates and co-ordinates all components there is no need for one component to know where the others are. In other words, if a component is displaced, only the broker unit 402 needs to be advised of the new location.

Yet another advantage is that the different components of the system may be distributed in different computing nodes and even be in remote geographical locations. For example, the labor progress unit 400 may be located in the main computing center of a hospital complex while the information gathering unit 404 may be located in the room of a patient in the obstetrics department. In other words, while the group of clinical measurements is collected in one location, calculations on the group of clinical measurements can be transparently performed in a completely different location. Consequently, a single labor progress unit 400 can be used for a set of patients in different rooms without requiring the displacement of the labor progress unit 400.

Yet another advantage of providing a system making use of a broker architectural pattern is that components may interact with one another over existing computer networks such as for example the Internet.

Figure 7:
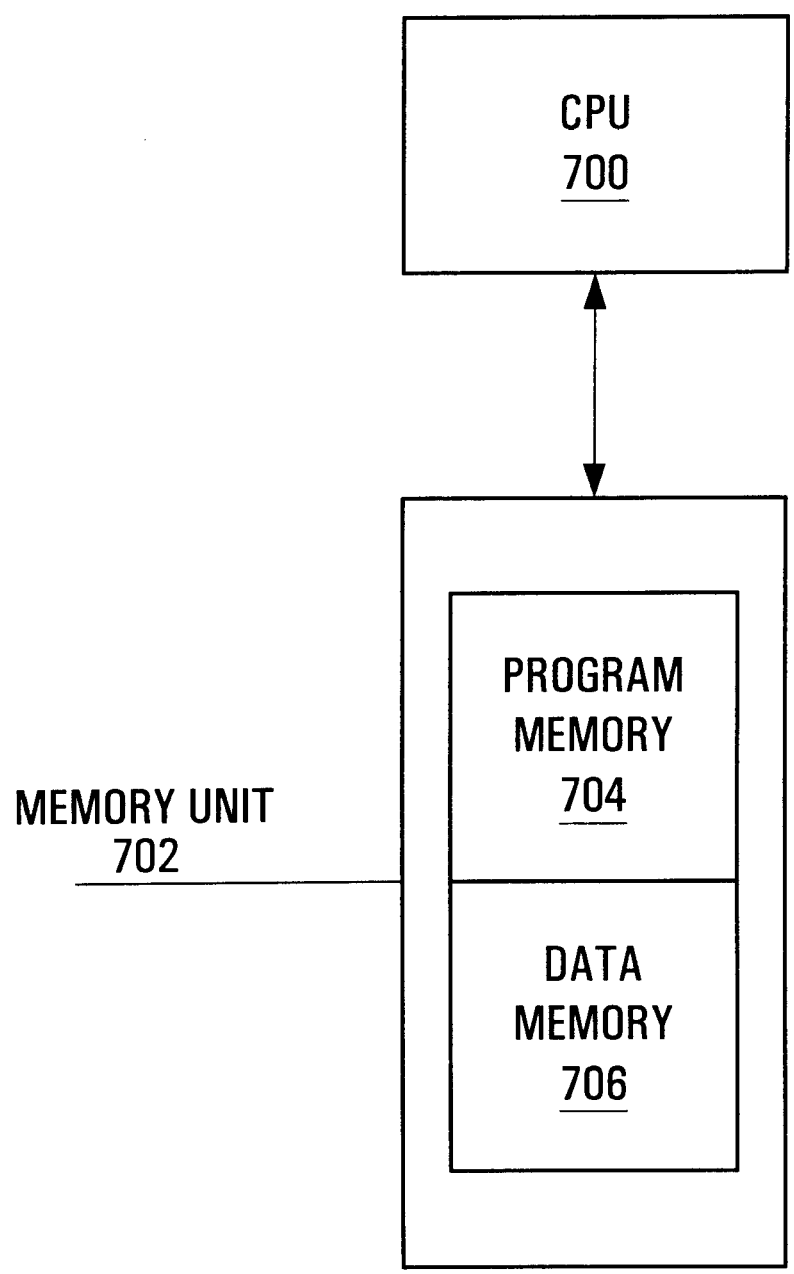
FIG. 7 is a block diagram of an apparatus for tracking the labor progress of a patient during childbirth in accordance with an alternative example of implementation.

The method described in the specification can also be implemented on any suitable computing platform as shown in FIG. 7. Such a computing platform typically includes a processor 700 and a memory unit or computer readable medium 702 connected to the processor 700 by a data communication bus. The memory stores the data 706 and the instructions of the program element 704 implementing the functional blocks depicted in the drawings and described in the specification. In a specific example, the program element 704 implements the processing unit 103 described in connection with FIG. 1. The program element 704 operates on the data 706 in accordance with the algorithms described above to generate a reference measure indicative of a certain expected dilatation of the cervix allowing assessing the progress of childbirth. In another specific example, the program element 704 is operative for implementing the broker unit 402 described in connection with FIG. 4. In yet another specific example, the program element 704 is operative for implementing the information gathering unit 404 described in connection with FIG. 4. In yet another specific example, the program element 704 is operative for implementing labor progress unit 400 described in connection with FIG. 4. The computing apparatus typically executes an operating system. A very specific example of implementation makes use of a general purpose digital computer running the Microsoft™ Windows NT™ operating system. Microsoft™ Windows NT™ may be used to integrate multiple components such as databases, messaging, Web portals and application packaging among others. Other operating systems may be used without detracting from the spirit of the invention.

Although the present invention has been described in considerable detail with reference to certain preferred embodiments thereof, variations and refinements are possible without departing from the spirit of the invention. Therefore, the scope of the invention should be limited only by the appended claims and their equivalents.

What is claimed is:

1. An apparatus for tracking the labor progress of a patient during childbirth, said apparatus comprising:

a) an input for receiving a group of clinical measurements associated to a patient, said group of clinical measurements including data elements indicative of a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth;

b) a processing unit coupled to said input, said processing unit being operative for generating a reference measure indicative of a certain expected dilatation of the cervix allowing to assess the progress of childbirth by using the following formula:

$$x = AA + BB*(1-y) + CC*z + DD*w + EE*v + FF*u$$

where:
x is the certain expected dilatation of the cervix;
y is the epidural status;
z is the previous dilatation of the cervix measurement;
w is the previous effacement measurement of the cervix;
v is the previous level of descent of the child;
u is the contraction count;
and where AA, BB, CC, DD, EE and FF are a set of real numbers conditioned at least in part on the basis of said parity status;

c) an output for releasing a signal indicative of a measurement of the certain expected dilatation of the cervix.

2. An apparatus as defined in claim 1, wherein when said parity status is indicative of a first childbirth, the set of real numbers is a first set of real numbers characterized by:
i. AA having a value of about 2.5;
ii. BB having a value of about 0.15;
iii. CC having a value of about 0.8;
iv. DD having a value of about 0.24;
v. EE having a value of about 0.04;
vi. FF having a value of about 0.004.

3. An apparatus as defined in claim 2, wherein the first set of real numbers is characterized by:
a) AA having a value of about 0.24952;
b) BB having a value of about 0.14627;
c) CC having a value of about 0.80515;
d) DD having a value of about 0.24109;
e) EE having a value of about 0.03909;
f) FF having a value of about 0.00447.

4. An apparatus as defined in claim 1, wherein when said parity status is indicative of a childbirth subsequent to a first childbirth, the set of real numbers is a second set of real numbers characterized by:
i. AA having a value of about 2;
ii. BB having a value of about 0.2;
iii. CC having a value of about 0.8;
iv. DD having a value of about 0.15;
v. EE having a value of about 0.2;
vi. FF having a value of about 0.01.

5. An apparatus as defined in claim 4, wherein the second set of real numbers is characterized by:
a) AA having a value of about 1.9914;
b) BB having a value of about 0.23484;
c) CC having a value of about 0.7770;
d) DD having a value of about 0.15503;
e) EE having a value of about 0.20669;
f) FF having a value of about 0.00766.

6. An apparatus as defined in claim 1, wherein said formula includes an error estimate data element indicative of a residual value, said error estimate allowing to derive a range of expected dilatations of the cervix having a normal distribution.

7. An apparatus as defined in claim 6, wherein said error estimate data element has a value of about 1.3.

8. An apparatus as defined in claim 7, wherein when said parity status is indicative of a first childbirth, the set of real numbers is a first set of real numbers characterized by:
a) AA having a value of about 0.024952;
b) BB having a value of about 0.14627;
c) CC having a value of about 0.80515;
d) DD having a value of about 0.24109;
e) EE having a value of about 0.03909;
f) FF having a value of about 0.00447;
and said error estimate has a value of about 1.3014.

9. An apparatus as defined in claim 7, wherein when said parity status is indicative of a childbirth subsequent to a first childbirth, the set of real numbers is a second set of real numbers characterized by:
a) AA having a value of about 1.9914;
b) BB having a value of about 0.23484;
c) CC having a value of about 0.7770;
d) DD having a value of about 0.15503;
e) EE having a value of about 0.20669;
f) FF having a value of about 0.00766;
and said error estimate has a value of about 1.3451.

10. An apparatus as defined in claim 6, wherein said group of clinical measurements includes a data element indicative of a current dilatation of the cervix measurement.

11. An apparatus as defined in claim 10, wherein said processing unit is operative for processing said current dilatation of the cervix measurement to derive a ranking data element indicative of a percentile ranking of the current dilatation of the cervix measurement with respect to the range of expected dilatation of the cervix on the basis of said certain expected dilatation of the cervix and said error estimate.

12. An apparatus as defined in claim 11, wherein said output further releases a signal indicative of the ranking data element.

13. An apparatus as defined in claim 6, wherein said processing unit is further operative to generate a plurality of expected dilatations of the cervix of defining a reference band of expected dilatations of the cervix, the reference band of expected dilatations of the cervix including said certain expected dilatation of the cervix, the reference band being a portion of said range of expected dilatations of the cervix.

14. An apparatus as defined in claim 13, wherein said output is further for releasing a signal indicative of the reference band of expected dilatations of the cervix.

15. An apparatus as defined in claim 14, wherein said input is for receiving a plurality of groups of clinical measurements, each group of clinical measurements being associated with a respective time, said processing unit being operative for processing the plurality of groups of clinical measurements to generate a sequence of certain expected dilatations of the cervix, said output being also operative for releasing a signal indicative of the sequence of certain expected dilatations of the cervix.

16. An apparatus as defined in claim 15, wherein said processing unit is further operative to generate a sequence of reference bands of expected dilatations of the cervix, said output being also operative for releasing a signal indicative of a graphical representation of the sequence of reference bands of expected dilatations of the cervix.

17. A method for tracking the labor progress of a patient during childbirth, said method comprising:

a) receiving a group of clinical measurements associated to a patient, said group of clinical measurements including data elements indicative of a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth;

b) generating a reference measure indicative of a certain expected dilatation of the cervix allowing to assess the progress of childbirth by using the following formula:

$$x=AA+BB*(1-y)+CC*z+DD*w+EE*v+FF*u$$

where:
x is the certain expected dilatation of the cervix;
y is the epidural status;
z is the previous dilatation of the cervix measurement;
w is the previous effacement measurement of the cervix;
v is the previous level of descent of the child;
u is the contraction count;
and where AA, BB, CC, DD, EE and FF are a set of real numbers conditioned at least in part on the basis of said parity status.

18. A method as defined in claim 17, wherein when said parity status is indicative of a first childbirth, the set of real numbers is a first set of real numbers characterized by:
i. AA having a value of about 2.5;
ii. BB having a value of about 0.15;
iii. CC having a value of about 0.8;
iv. DD having a value of about 0.24;
v. EE having a value of about 0.04;
vi. FF having a value of about 0.0004.

19. A method as defined in claim 18, wherein the first set of real numbers is characterized by:
a) AA having a value of about 0.24952;
b) BB having a value of about 0.14627;
c) CC having a value of about 0.80515;
d) DD having a value of about 0.24109;
e) EE having a value of about 0.03909;
f) FF having a value of about 0.00447.

20. A method as defined in claim 17, wherein when said parity status is indicative of a childbirth subsequent to a first childbirth, the set of real numbers is a second set of real numbers characterized by:
i. AA having a value of about 2;
ii. BB having a value of about 0.2;
iii. CC having a value of about 0.8;
iv. DD having a value of about 0.15;
v. EE having a value of about 0.2;
vi. FF having a value of about 0.01.

21. A method as defined in claim 21, wherein the second set of real numbers is characterized by:
a) AA having a value of about 1.9914;
b) BB having a value of about 0.23484;
c) CC having a value of about 0.7770;
d) DD having a value of about 0.15503;
e) EE having a value of about 0.20669;
f) FF having a value of about 0.00766.

22. A method as defined in claim 17, wherein said formula includes an error estimate data element indicative of a residual value, said method further comprising generating a range of expected dilatations of the cervix having a normal distribution on the basis of said error estimate.

23. A method as defined in claim 22, wherein said error estimate data element has a value of about 1.3.

24. A method as defined in claim 23, wherein when said parity status is indicative of a first childbirth, the set of real numbers is a first set of real numbers characterized by:
a) AA having a value of about 0.24952;
b) BB having a value of about 0.14627;
c) CC having a value of about 0.80515;
d) DD having a value of about 0.24109;
e) EE having a value of about 0.03909;
f) FF having a value of about 0.00447;
and said error estimate has a value of about 1.3014.

25. A method as defined in claim 23, wherein when said parity status is indicative of a childbirth subsequent to a first childbirth, the set of real numbers is a second set of real numbers characterized by:
a) AA having a value of about 1.9914;
b) BB having a value of about 0.23484;
c) CC having a value of about 0.7770;
d) DD having a value of about 0.15503;
e) EE having a value of about 0.20669;
f) FF having a value of about 0.00766;
and said error estimate has a value of about 1.3451.

26. A method as defined in claim 22, wherein said group of clinical measurements includes a data element indicative of a current dilatation of the cervix measurement.

27. A method as defined in claim 26, wherein said method further comprises processing said current dilatation of the cervix measurement to derive a ranking data element indicative of a percentile ranking of the current dilatation of the cervix measurement with respect to the range of expected dilatations of the cervix on the basis of said certain expected dilatation of the cervix and said error estimate.

28. A method as defined in claim 27, further comprising using the signal indicative of the ranking data element for assisting in the determination of whether a cesarean delivery is required for the patient.

29. A method a as defined in claim 22, wherein said method further comprises generating a plurality of expected dilatations of the cervix defining a reference band of expected dilatations of the cervix, the reference band of expected dilatations of the cervix including said certain expected dilatation of the cervix, the reference band being a portion of said range of expected dilatations of the cervix.

30. A method as defined in claim 29, wherein said method further comprises:
a) receiving a plurality of groups of clinical measurements, each group of clinical measurements being associated with a respective time;
b) processing the plurality of groups of clinical measurements to generate a sequence of certain expected dilatations of the cervix.

31. A method as defined in claim 30, wherein said method further comprises generating a sequence of reference bands of expected dilatations of the cervix.

32. A computer readable medium comprising a program element suitable for execution by a computing apparatus for tracking the labor progress of a patient during childbirth, said computing apparatus including a processor, said program element when executing on said processor being operative for implementing:
i. an input unit for receiving a group of clinical measurements associated to a patient, said group of clinical measurements including data elements indicative of a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth;
ii. a processing unit for generating a reference measure indicative of a certain expected dilatation of the cervix allowing to assess the progress of childbirth by using the following formula:

$$x=AA+BB*(1-y)+CC*z+DD*w+EE*v+FF*u$$

where:
x is the certain expected dilatation of the cervix;
y is the epidural status;
z is the previous dilatation of the cervix measurement;
w is the previous effacement measurement of the cervix;
v is the previous level of descent of the child;
u is the contraction count;
and where AA, BB, CC, DD, EE and FF are a set of real numbers conditioned at least in part on the basis of said parity status.

33. A broker unit suitable for use in interconnecting components of a system for tracking the labor progress of a patient during childbirth, the system including:
   a) an information gathering unit associated to a first entity identifier, the information gathering unit being suitable for receiving a group of clinical measurements associated to a patient;
   b) a labor progress unit associated to a second entity identifier, the labor progress unit being operative for generating a reference measure indicative of a certain expected dilatation of the cervix allowing to assess the progress of childbirth;
   said broker unit comprising:
      i. a first communication port suitable for exchanging messages with the information gathering unit, each message including a destination entity identifier;
      ii. a second communication port suitable for exchanging messages with the labor progress unit, each message including a destination entity identifier;
      iii. a processor operative for processing a certain message received from the information gathering unit at the first communication port such as to forward it to the second communication port for transmission to the labor progress unit when the certain message includes a destination entity identifier matching the second entity identifier.

34. A broker unit as defined in claim 33, wherein said processor is further operative for processing a certain message received from the labor progress unit at the second communication port such as to forward it to the first communication port for transmission to the information gathering unit when the certain message includes a destination entity identifier matching the first entity identifier.

35. A broker unit as defined in claim 34, wherein the first communication port is further suitable for exchanging messages with a set of information gathering units, each information gathering unit in the set of information gathering units being associated with a respective first entity identifier; said broker unit further comprising:
   a) a data structure including a plurality of entries, at least one entry being associated to the labor progress unit, the at least one entry including a subscriber list suitable for storing at least one first entity identifier associated to a certain information gathering unit from the set of information gathering units;
   b) said processor being further operative for processing a certain message received from the labor progress unit at the second communication port such as to forward it to the first communication port for transmission to the certain information gathering unit associated to the at least one first entity identifier.

36. A broker unit as defined in claim 35, wherein the subscriber list is suitable for storing a plurality of first entity identifiers associated to respective ones of the set of information gathering units;
   a) said processor being further operative for processing a certain message received from the labor progress unit at the second communication port such as to forward it to the first communication port for transmission to the respective ones of the set of information gathering units associated to a plurality of first entity identifiers.

37. A system for tracking the labor progress of a patient during childbirth, the system including:
   a) an information gathering unit associated to a first entity identifier, the information gathering unit being suitable for receiving a group of clinical measurements associated to a patient;
   b) a labor progress unit associated to a second entity identifier, the labor progress unit being operative for generating a reference measure indicative of a certain expected dilatation of the cervix allowing to assess the progress of childbirth;
   c) a broker unit comprising:
      i. a first communication port suitable for exchanging messages with the information gathering unit, each message including a destination entity identifier;
      ii. a second communication port suitable for exchanging messages with the labor progress unit, each message including a destination entity identifier;
      iii. a processor operative for processing a certain message received from the information gathering unit at the first communication port such as to forward it to the second communication port for transmission to the labor progress unit when the certain message includes a destination entity identifier matching the second entity identifier.

38. A system as defined in claim 37, wherein said processor of the broker unit is further operative for processing a certain message received from the labor progress unit at the second communication port such as to forward it to the first communication port for transmission to the information gathering unit when the certain message includes a destination entity identifier matching the first entity identifier.

39. A system as defined in claim 38, comprising a set of information gathering units, each information gathering unit of said set of information gathering units being associated with a respective first entity identifier, the first communication port of the broker unit being further suitable for exchanging messages with each information gathering unit of the set of information gathering units.

40. A system as defined in claim 39, wherein said broker unit further comprises:
   a) a data structure including a plurality of entries, at least one entry being associated to the labor progress unit, the at least one entry including a subscriber list suitable for storing at least one first entity identifier associated to a certain information gathering unit from the set of information gathering units;
   b) the processor of the broker unit being further operative for processing a certain message received from the labor progress unit at the second communication port such as to forward it to the first communication port for transmission to the certain information gathering unit associated to the at least one first entity identifier.

41. A system as defined in claim 40, wherein the subscriber list is suitable for storing a plurality of first entity identifiers associated to respective ones of the set of information gathering units, said processor of the broker unit being further operative for processing a certain message received from the labor progress unit at the second communication port such as to forward it to the first communication port for transmission to the respective ones of the set of information gathering units associated to the plurality of first entity identifiers.

42. A system as defined in claim 37, wherein:
a) the information gathering unit is located at a primary site;
b) the labor progress unit is located at a secondary site.

43. A system as defined in claim 42, wherein the primary site is located on a comprising node.

44. A system as defined in claim 43, wherein the computing node is a first computing node and wherein said secondary site is located on a second computing node.

45. A system as defined in claim 47, wherein said group of clinical measurements including data elements indicative of a measurement of previous dilation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth.

46. A system as defined in claim 45, wherein the labor progress unit is operative for generating the reference measure indicative of the certain expected dilatation of the cervix by using a formula of the form:

$$x=AA+BB*(1-y)+CC*z+DD*w+EE*v+FF*u$$

where:
x is the certain expected dilatation of the cervix;
y is the epidural status;
z is the previous dilatation of the cervix measurement;
w is the previous effacement measurement of the cervix;
v is the previous level of descent of the child;
u is the contraction count;
and where AA, BB, CC, DD, EE and FF are a set of real numbers conditioned at least in part on the basis of said parity status.

47. An apparatus for tracking the labor progress of a patient during childbirth, said apparatus comprising:
a) means for receiving a group of clinical measurements associated to a patient, said group of clinical measurements including data elements indicative of a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth;
b) means for generating a reference measure indicative of a certain expected dilatation of the cervix allowing to assess the progress of childbirth by using the following formula:

$$x=AA+BB*(1-y)+CC*z+DD*w+EE*v+FF*u$$

where:
x is the certain expected dilatation of the cervix;
y is the epidural status;
z is the previous dilatation of the cervix measurement;
w is the previous effacement measurement of the cervix;
v is the previous level of descent of the child;
u is the contraction count;
and where AA, BB, CC, DD, EE and FF are a set of real numbers conditioned at least in part on the basis of said parity status;
c) means for releasing a signal indicative of a measurement of the certain expected dilatation of the cervix.

48. A computer data signal embodied in a transmission medium comprising:

i. a clinical measurement collection source code segment comprising a first program element suitable for execution on a computing apparatus, said first program element when executing on said processor being operative for implementing an information gathering unit, the information gathering unit being suitable for receiving a group of clinical measurements associated to a patient, said group of clinical measurements including data elements indicative of a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth;

b) a labor tracking source code segment comprising a second program element suitable for execution on a computing apparatus, said second program element when executing on said processor being operative for implementing a labor progress unit, the labor progress unit being operative for generating a reference measure indicative of a certain expected dilatation of the cervix allowing to assess the progress of childbirth by using the following:

$$x=AA+BB*(1-y)+CC*z+DD*w+EE*v+FF*u$$

where:
x is the certain expected dilatation of the cervix;
y is the epidural status;
z is the previous dilation of the cervix measurement;
w is the previous effacement measurement of the cervix;
v is the previous level of descent of the child;
u is the contraction count; and where AA, BB, CC, DD, EE and FF are a set of real numbers conditioned at least in part on the basis of said parity status, the labor progress unit being operative for releasing a signal indicative of a measure of the certain expected dilatation of the cervix.

49. An apparatus for tracking the labor progress of a patient during childbirth, said apparatus comprising:
a) an input for receiving a group of clinical measurements associated to a patient during childbirth and a data element indicative of a current dilatation of the cervix measurement;
b) a processing unit coupled to said input, said processing unit being operative for:
i. processing the group of clinical measurements on the basis of an error estimate to derive a range of expected dilatations of the cervix, and
ii. processing the current dilatation of the cervix measurement to derive ranking data indicative of a percentile ranking of the current dilatation of the cervix measurement with respect to the range of expected dilatations of the cervix; and
c) an output for releasing the ranking data.

50. An apparatus as defined in claim 49, wherein said group of clinical measurements includes a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth.

51. A method for tracking the labor progress of a patient during childbirth, said method comprising:

a) receiving a group of clinical measurements associated to a patient during childbirth and a data element indicative of a current dilatation of the cervix measurement;

b) processing the group of clinical measurements on the basis of an error estimate to derive a range of expected dilatations of the cervix;

c) processing the current dilatation of the cervix measurement to derive ranking data indicative of a percentile ranking of the current dilatation of the cervix measurement with respect to the range of expected dilatations of the cervix;

d) releasing the ranking data; and e) using the ranking data to assist in the determination of whether a cesarean delivery is required for the patient.

52. A method as defined in claim 51, wherein said group of clinical measurements includes a measurement of a previous dilatation of the cervix of the patient, a contraction count, a previous level of descent of the child, a previous effacement measurement of the cervix, an epidural status and a parity status, said parity status being indicative of either one of a first childbirth for the patient and a childbirth subsequent to a first childbirth.

* * * * *

UNITED STATES PATENT AND TRADEMARK OFFICE
CERTIFICATE OF CORRECTION

PATENT NO. : 6,423,016 B1
DATED : July 23, 2002
INVENTOR(S) : Emily Hamilton, Mario Boisclair, Ebi Kimanani and Bruno Bendavid It is certified that error appears in the above-identified patent and that said Letters Patent is hereby corrected as shown below:

Column 15,
Line 24, delete "0.0004" and insert -- 0.004 --;
Line 43, delete "21" and insert -- 20 --;

Column 19,
Line 10, delete "47" and insert -- 37 --;
Line 12, insert -- a -- between "of" and "previous";

Column 20,
Line 25, insert -- formula -- after the word "following".

Signed and Sealed this

Twenty-fourth Day of December, 2002

JAMES E. ROGAN
*Director of the United States Patent and Trademark Office*